US012623065B2

(12) United States Patent
Fuchs et al.

(10) Patent No.: US 12,623,065 B2
(45) Date of Patent: May 12, 2026

(54) SYSTEM COMPRISING A CAP FOR A MEDICAL FLUID CONTAINER AND AN ATTACHMENT PART, MEDICAL FLUID CONTAINER, AND METHOD FOR PRODUCING A FLUID CONTAINER

(71) Applicant: B. Braun Melsungen AG, Melsungen (DE)

(72) Inventors: Juergen Fuchs, Bad Emstal (DE); Juergen Hartung, Helsa (DE)

(73) Assignee: B. Braun Melsungen AG, Melsungen (DE)

( * ) Notice: Subject to any disclaimer, the term of this patent is extended or adjusted under 35 U.S.C. 154(b) by 649 days.

(21) Appl. No.: 18/012,375

(22) PCT Filed: Jun. 28, 2021

(86) PCT No.: PCT/EP2021/067723
§ 371 (c)(1),
(2) Date: Dec. 22, 2022

(87) PCT Pub. No.: WO2022/002863
PCT Pub. Date: Jan. 6, 2022

(65) Prior Publication Data
US 2023/0248957 A1 Aug. 10, 2023

(30) Foreign Application Priority Data
Jun. 30, 2020 (DE) ..................... 10 2020 208 146.8

(51) Int. Cl.
*A61M 39/10* (2006.01)
*A61J 1/14* (2023.01)
(Continued)

(52) U.S. Cl.
CPC ............ *A61M 39/10* (2013.01); *A61J 1/1406* (2013.01); *A61J 1/1468* (2015.05); *A61J 1/1481* (2015.05);
(Continued)

(58) Field of Classification Search
CPC ...... A61J 1/1406; A61J 1/1475; A61J 1/1481; A61J 1/201; A61J 1/2037; A61J 1/1412;
(Continued)

(56) References Cited

U.S. PATENT DOCUMENTS 5,678,713 A * 10/1997 Derksen ................ A61J 1/1406
215/254
6,681,946 B1 1/2004 Jansen et al.
(Continued)

FOREIGN PATENT DOCUMENTS

DE 102007005407 A1 8/2008
DE 102007024539 A1 11/2008
(Continued)

OTHER PUBLICATIONS

Search Report received in International Application No. PCT/EP2021/067723 dated Oct. 12, 2021, with translation, 13 pages.

*Primary Examiner* — Ariana Zimbouski
(74) *Attorney, Agent, or Firm* — Christopher A. Rothe; CM Law

(57) ABSTRACT
A system includes a cap for a medical fluid container and an attachment part. The cap includes at least one first port. The first port includes a septum and a connection structure. The attachment part includes a hollow spike and a joining structure in fluid communication with the hollow spike. The joining structure is configured for connecting the device for withdrawing fluid from the fluid container and/or for supplying fluid into the fluid container. The connection structure is configured to be connected to a complementary connec-
(Continued)

tion structure of the attachment part in a releasable or non-releasable manner such that the hollow spike of the attachment part pierces the septum.

19 Claims, 3 Drawing Sheets

(51) Int. Cl.
  *A61J 1/20*     (2006.01)
  *B65D 51/00*     (2006.01)
(52) U.S. Cl.
  CPC ............. *A61J 1/201* (2015.05); *A61J 1/2037* (2015.05); *B65D 51/002* (2013.01)
(58) Field of Classification Search
  CPC ......... A61J 1/20; B65D 51/002; B65D 51/22; B65D 47/36; B65D 41/50; A61M 5/1411; A61M 2039/1033; A61M 39/12
  See application file for complete search history.

(56)      References Cited

U.S. PATENT DOCUMENTS

| | | | |
|---|---|---|---|
| 11,351,090 B2 | 6/2022 | Brandenburger et al. | |
| 2007/0106244 A1* | 5/2007 | Mosler .................. | A61J 1/2096 |
| | | | 604/407 |

| | | | | |
|---|---|---|---|---|
| 2008/0262466 A1* | 10/2008 | Smith .................. | B65D 51/002 | |
| | | | 215/247 | |
| 2010/0059474 A1 | 3/2010 | Brandenburger et al. | | |
| 2010/0163448 A1* | 7/2010 | LaValley .............. | B65D 51/002 | |
| | | | 206/524.5 | |
| 2010/0308056 A1 | 12/2010 | Brandenburger et al. | | |
| 2011/0004184 A1 | 1/2011 | Proksch et al. | | |
| 2011/0245796 A1 | 10/2011 | Brandenburger et al. | | |
| 2013/0037509 A1* | 2/2013 | Rahimy ................ | A61J 1/1418 | |
| | | | 215/250 | |
| 2014/0311617 A1* | 10/2014 | Py ......................... | A61J 1/1425 | |
| | | | 141/89 | |
| 2015/0305977 A1 | 10/2015 | Spallek et al. | | |
| 2018/0125755 A1* | 5/2018 | Spallek ................... | A61J 1/06 | |

FOREIGN PATENT DOCUMENTS

| | | |
|---|---|---|
| DE | 102007046951 B3 | 2/2009 |
| DE | 102008060864 A1 | 6/2010 |
| DE | 102012021525 A1 | 4/2014 |
| DE | 102014226900 A1 | 6/2016 |
| EP | 1010412 A2 | 6/2000 |
| EP | 1616808 A1 | 1/2006 |
| EP | 1955964 A1 | 8/2008 |
| WO | 2006005391 A1 | 1/2006 |
| WO | 2016156242 A1 | 10/2016 |
| WO | 2019238773 A1 | 12/2019 |

* cited by examiner

SYSTEM COMPRISING A CAP FOR A MEDICAL FLUID CONTAINER AND AN ATTACHMENT PART, MEDICAL FLUID CONTAINER, AND METHOD FOR PRODUCING A FLUID CONTAINER

CROSS-REFERENCE TO RELATED APPLICATIONS

This application is the United States national stage entry of International Application No. PCT/EP2021/067723, filed Jun. 28, 2021, and claims priority to German Application No. 10 2020 208 146.8, filed Jun. 30, 2020. The contents of International Application No. PCT/EP2021/067723 and German Application No. 10 2020 208 146.8 are incorporated by reference herein in their entireties.

BACKGROUND

Infusions and transfusions are performed for therapeutic purposes in human and veterinary medicine. For example, infusions are used to administer liquids (e.g. active substance solutions or other liquid pharmaceuticals) into the bloodstream of a patient. For this purpose, the liquid to be administered is taken from a liquid container and flows through an infusion set (also called an "intravenous set" or "I. V. set") to the patient access. The fluid enters the patient's bloodstream through the patient access. The patient access may be, for example, a venous cannula or a venous catheter.

An infusion or transfusion set comprises a tube. Often, but not necessarily, the infusion or transfusion set has a drip chamber connected to the tube such that the fluid flows through the drip chamber into the tube. The infusion or transfusion set may optionally include other components, such as a flow regulator to control the rate of flow of the fluid, e.g. a roller clamp.

If a drip chamber is provided, the drip chamber is connected to the container via a container connector such that fluid can pass from the container into the drip chamber. Otherwise, the tube is provided with such a container connector.

The container connector may, for example, be a piercing device, such as a hollow mandrel which can be used to pierce a septum of the container and which has one or more fluid channels in its interior. Such a piercing device is commonly referred to as a "spike". Other systems are also known for connecting the infusion or transfusion set to the container, for example coupling systems with plug-in connections.

A "septum" is understood to be a container closure comprising a rubber membrane or a membrane made of another suitable elastic material. The membrane is pierced with a hollow piercing device to remove a fluid from the container or to introduce a fluid into the interior of the container. The piercing device may be the spike already described above, a cannula, a hypodermic needle, etc. The membrane is self-sealing, i.e. when the piercing device is withdrawn from the membrane again, the opening pierced by the piercing device closes at least partially, preferably completely. Accordingly, the membrane of a septum does not have a prefabricated opening in the form of a hole or slit into which the piercing device is inserted.

A "fluid" is understood to mean a flowable material, in particular a liquid, a gas, a suspension or an aerosol.

A container access is commonly referred to as a "port" in the case of medical fluid containers. Accordingly, the port is the area of the container to which an external device for fluid withdrawal or fluid addition is connected in order to establish fluid communication between the interior of the container and the external device.

"Medical fluid containers" are understood to be containers that are intended to contain medical fluids and are made of a material suitable for this purpose. Medical fluids are, for example, liquid pharmaceuticals, liquid pharmaceutical components and blood for transfusion purposes.

The liquid container from which the liquid to be administered is taken can be a bottle made of a rigid material such as glass. In addition, plastic bottles with a certain flexibility or plastic bags have become established on the market. Plastic not only has the advantage of having a lower specific weight and being less fragile than glass. If a sufficiently flexible plastic is used, another advantage is that the container collapses when liquid is removed from it. This means that the volume of the container interior continuously adapts to the decreasing volume of the liquid contained therein such that no additional provisions for pressure equalisation in the form of an air inflow channel or an air inflow opening are required, which not only simplifies the design but also avoids the risk of contamination of the container interior by inflowing air.

Some of the containers for infusion fluids available on the market allow the addition of other medicines (so-called "pharmacy admixture"). Admixture is done, for example, by injection through another port on the container, which also has a septum. "Injecting" is understood to mean injecting by means of an injection syringe equipped with an injection needle, whereby the injection needle is pierced through the septum. Typically, this further port is located at a point on the container close to the position of the port via which the container connector of the infusion or transfusion set is connected to the container. By having multiple ports, fluid can be withdrawn and added at the same time. This makes it possible to add a pharmaceutical while the infusion is being carried out.

Containers for infusion fluids that have a cap on the container head, which points downwards during infusion, and that are made of a polyolefin material are known in the prior art and available on the market, wherein the cap has two ports located next to each other. A cap of this type is also called a "twin port cap". The two ports are of the same design and each allows the puncture of a septum by a spike and the injection using a hypodermic syringe equipped with a hypodermic needle. When piercing a septum, the container wall underneath the septum is pierced at the same time. Therefore, the containers described have the advantage that they are not sealed by a septum, but that the container wall per se is closed and securely seals the contents of the container before a septum and thus the container wall has been pierced for the first time by a piercing device. This also provides an advantage in terms of production technology because the cap is placed on the already closed container. For example, the present applicant offers such containers under the registered trademark ECOFLAC® plus.

The disadvantage of injecting with a hypodermic syringe equipped with a hypodermic needle is the inconvenient handling, because a suitable hypodermic needle has to be kept in stock, unpacked, connected to the hypodermic syringe and then disposed of. Another disadvantage is that piercing with the injection needle is prone to errors. In particular, if the piercing is not vertical to the septum, the injection needle may bend and/or the septum may not seal completely after the injection needle is withdrawn. A further disadvantage is that handling a hypodermic needle involves a potential risk of injury. The aforementioned disadvantages apply all the more if the injection is to take place during the infusion, as the container is then positioned upside down and the port for injection is therefore difficult to access. It is also disadvantageous that with the conventional approach, the hypodermic needle is only held in the area of the puncture by contact with the septum such that it can be pulled out or fall out unintentionally. The disadvantages mentioned are further aggravated if the injection procedure is to be carried out very quickly due to the circumstances.

From DE 10 2007 005 407 A1, a closure cap for a container for containing medical liquids is known, which has an injection portion and a withdrawal portion. The withdrawal portion has a pierceable membrane through which a spike of an infusion set can be pierced in a conventional manner. The injection portion is configured to receive the male cone of an injection syringe. The injection portion does not have a septum, but a slit valve, i.e. a membrane with a slit which is opened by the inserted male syringe cone. Although the closure cap of DE 10 2007 005 407 A1 allows the needleless connection of an injection syringe to the injection portion, it is not possible to connect a piercing device such as a spike to the injection portion. Furthermore, it is not possible to place the cap of DE 10 2007 005 407 A1 on a container with a closed container wall, because the syringe cone would not be suitable to pierce a container wall located underneath the slit valve. As a result, a container according to DE 10 2007 005 407 A1 has an opening that is sealed from the environment only by the slit valve. A slit valve is prone to leakage, especially if there is overpressure in the container or the container is upside down. Apart from a possible undesired loss of liquid, contamination may enter through the slit valve. According to DE 10 2007 005 407 A1, the injection portion is closed with a break-off part. This break-off part is costly in terms of production technology and cumbersome in terms of handling. In addition, the function of the break-off part is no longer available if it has been broken off by the user as intended.

SUMMARY

Based on the above-mentioned situation, it is a task of the invention to provide an improved system comprising a cap for a medical fluid container and an attachment part as well as an improved medical fluid container, in particular an improved container for an infusion liquid. In particular, this is intended to enable or improve the needle-free addition or removal of fluid from the container, i.e. the addition or removal without the use of a separate piercing device.

The system according to the invention is a system comprising a cap for a medical fluid container and an attachment part. In particular, the cap is a cap for a container for a medical liquid. The cap has at least a first port for providing a fluid connection between the fluid container and an external device. The external device is a device for withdrawing fluid from the fluid container and/or a device for supplying fluid to the fluid container. For example, the external device is a hypodermic syringe. The first port comprises a septum. As mentioned above, a septum comprises a self-sealing membrane made of a suitable elastic material such as rubber or the like. The membrane is pierced with a hollow piercing device in order to remove a fluid from the container or to introduce a fluid into the interior of the container. The first port additionally has a connection structure. The attachment part comprises a hollow spike and a joining structure in fluid communication with the hollow spike. The joining structure is configured to connect a device for withdrawing fluid from the fluid container and/or a device for supplying fluid to the fluid container. The connection structure is configured to be connected to a complementary connection structure of the attachment part in a releasable or non-releasable manner such that the hollow spike of the attachment part pierces the septum.

The aforementioned port is referred to as the "first port" even if the cap has only a single port.

A "releasable connection" between two elements is understood to be a reversible connection, i.e. a connection that can be separated again without thereby destroying the elements. Examples are plug-in connections, screw connections and reversible engagement connections. Conversely, a "non-releasable connection" is understood to be an irreversible connection. An example thereof is an irreversible engagement connection.

In that, according to the present invention, the first port comprises a connection structure, it is possible to connect the attachment part to the first port, wherein the hollow spike of the attachment part thereby pierces the septum of the first port. In this way it is possible to provide fluid communication between the interior of a container to which the cap is attached and the hollow spike. As the hollow spike is in fluid communication with a joining structure, fluid communication between the interior of the container and the joining structure is provided in this way. Fluid communication between the external device and the interior of the container may be provided via the joining structure without the need to pierce the septum of the first port by a piercing device of the external device. In other words, fluid communication between the fluid container and a device for withdrawing fluid from the fluid container and/or a device for introducing fluid into the fluid container is indirectly provided via the attachment part. In this sense, the attachment part can be understood as an adapter.

According to the invention, an external device does not necessarily have a piercing device in order to be connected to the container. In this way, for example, the handling when introducing a liquid into the container is significantly simplified and made safer. For example, to add a liquid provided in a syringe, there is no need to keep a separate hypodermic needle in stock, unpack it, connect it to the syringe and then dispose of it. Furthermore, handling errors that can occur when piercing with a hypodermic needle, such as not piercing vertically with respect to the septum, will be avoided. Furthermore, the risk of injury associated with handling a hypodermic needle is avoided. The aforementioned advantages of the invention are especially effective if the addition is to take place during infusion because the container is then arranged upside down and the port for injection is therefore difficult to access. The aforementioned advantages of the invention are also particularly effective if the addition shall take place several times and/or if the addition process shall take place quickly due to the circumstances. Furthermore, the connection structure enables a secure connection to the attachment part and thus a secure connection to the external device such that it can be avoided in the best possible way that the hollow spike is unintentionally pulled out.

Herein, the joining structure according to the invention not only enables fluid connection to be made with a device for supplying fluid to the container, but in the same way also enables fluid connection to be made with a device for withdrawing fluid from the container. For example, infusion sets are known which have a coupling structure instead of a spike which is not configured to pierce a septum. If the coupling structure of such an infusion set and the joining structure are complementary to each other, i.e. if the coupling structure and the joining structure can be connected to each other to form a fluid connection, the infusion set can be connected to the container without requiring the septum to be pierced separately. It is also possible to connect to the joining structure a tube or pipe having a structure complementary to the joining structure in order to transfer the contents of a container to which the cap of the system according to the invention is attached partially or completely to another container through the tube or pipe.

The invention further enables that, when piercing the septum of the first port with the hollow spike of the attachment part, the wall of the container to which the cap of the system according to the invention is attached is simultaneously pierced in the area located underneath the septum of the first port. The invention therefore provides particularly advantageous effects if the cap of the system according to the invention is used together with a container whose wall is made of a plastic material and is closed in itself such that the contents of the container are securely sealed.

Since the first port of the cap of the system according to the invention has a septum, the container to which the cap is attached is sterile and particularly securely sealed for transport and storage before the attachment part is attached or, optionally, after the attachment part has been removed. Preferably, the septum of the first port is covered in a sterile manner by a cover during transport and storage of the container to which the cap is attached. A suitable cover is, for example, a sealing foil such as a foil made of metal and/or plastic. The cover can ensure that the septum of the first port is also sterile on the side facing away from the container such that it does not have to be disinfected in a separate step before being pierced with the hollow spike of the attachment part.

In addition to the aforementioned advantages provided by the present invention, the cap of the system according to the invention allows an external device to be connected directly to the first port instead of the attachment part. For example, a spike of an infusion device can be pierced through the septum of the first port. Or a hypodermic needle can be pierced through the septum of the first port. In this way, the invention ensures the greatest possible flexibility, since a container to which the cap of the system according to the invention is connected can be universally used together with a variety of different external devices for fluid withdrawal or fluid addition. However, by additionally comprising the attachment part, the system according to the invention enables a versatile use of a fluid container.

Preferably, fluid communication between the interior of the container and the joining structure is enabled by having a continuous fluid channel in the attachment part extending from a distal end of the hollow spike to a proximal end of the joining structure. In this way, the function of the attachment part can be provided in a structurally simple and safe manner. Further preferably, because it is constructively particularly simple, a single fluid channel is provided, which is particularly useful if the container used is made of a flexible material such that a pressure equalisation channel is not required.

The positional designations "distal" and "proximal" are defined as follows: The distal end of the hollow spike is its tip. In other words, the distal end of the hollow spike is the end pointing into the interior of the container when the hollow spike has been pierced through the septum of the first port of the cap attached to the container. The proximal end of the joining structure is the end of the joining structure that is located further apart from the cap or container when the attachment part is connected to the cap.

In a preferred embodiment of the invention, the connection structure of the cap of the system according to the invention has a Luer cone, which provides a connection structure that can be handled easily and quickly and is compatible with a wide range of applications. So-called Luer connections are standardised connections intended for use in injection and infusion technology and related medical fields. The fluid connection between the elements to be connected is achieved by means of a conical construction of the connection portions, which are referred to as a "Luer cone". The internal Luer cone of one side of the connection is also referred to as "female", and the external Luer cone of the opposite side is also referred to as "male". In one variant, the external cone is simply inserted into the internal cone, without any structures being provided to secure the connection. This variant is called "Luer attachment", "Luer plug" or "Luer slip". In another variant, the external cone is provided with an internal thread and the internal cone is provided with a complementary external thread in order to lock the connection. This variant is called "Luer lock". The Luer system allows easy and quick handling and guarantees compatibility between different elements to be connected, even if they originate from different manufacturers. The Luer technique is standardised by ISO 80369-7.

It is preferred that the Luer cone of the connection structure is a female Luer cone. When using a female Luer cone in the connection structure of the cap, for example a sterile sealing of the relevant surface regions can be realised in a particularly simple manner by means of a foil.

Optionally or alternatively, it is preferred that the connection structure is a Luer lock type connection structure. This enables, for example, a secure connection between the cap and the attachment part.

In a preferred embodiment of the invention, the cap has a second port in addition to the first port described above, wherein the second port is separate from and preferably adjacent to the first port and also has a self-sealing septum. Herein, the second port may optionally have a connection structure analogous to the connection structure of the first port described above, such that it may also be connected to an attachment part of the type described above.

In further embodiments of the invention, the cap comprises three or more than three ports.

The attachment part of the system according to the invention comprises a hollow spike and a joining structure in fluid communication with the hollow spike. The joining structure is configured to connect a device for withdrawing fluid from the fluid container and/or a device for supplying fluid to the fluid container.

The attachment part of the system according to the invention contributes to achieving the effects and advantages of the present invention described above.

In a preferred embodiment, the joining structure of the attachment part comprises a valve. This allows, for example, the container to which the cap of the system according to the invention is attached to be sealed even when the cap is connected to the attachment part and therefore the hollow spike of the attachment part pierces the septum of the first port and when no device for withdrawing fluid from the fluid container and/or for supplying fluid to the fluid container is connected to the joining structure. The valve is further preferably a structurally particularly simple slit valve.

A system according to the invention comprises the cap and the attachment part.

The medical fluid container according to the invention is a medical fluid container, in particular for a medical liquid, comprising a hollow body and a system according to the invention.

In a preferred embodiment of the medical fluid container according to the invention, the hollow body is sealed in a fluid-tight manner. That is, the container wall is closed in itself (and is not sealed by a septum) before the container wall has been pierced for the first time by a piercing device. This results in the above-mentioned advantages in a particularly advantageous manner.

In another preferred embodiment of the medical fluid container according to the invention, the hollow body is collapsible. This results in the advantages mentioned above in this context in a particularly advantageous manner.

The method according to the invention is a method for manufacturing a fluid container, in particular a medical fluid container according to the invention. The method according to the invention comprises the steps:

providing a hollow body, preferably a hollow body filled with fluid, more preferably a hollow body filled with fluid and sealed in a fluid-tight manner, forming a cap of a system according to the invention on a region of the hollow body by injection moulding.

The method according to the invention optionally comprises, as a further step, forming the septum of the first port by injection moulding. The method according to the invention optionally comprises, as a further step, forming the septum of the second port by injection moulding.

Forming the cap by injection moulding, for example, offers the advantage of the best possible process consistency and process control compared to a welding process, which would be an alternative process step.

In a preferred embodiment of the process according to the invention, for providing the hollow body, a fluid-filled and fluid-tightly sealed hollow body is produced by means of the blow-fill-seal technique. In other words, according to this preferred embodiment, the production of the hollow body by means of the blow-fill-seal technique is part of the production of the method for producing a fluid container.

The basic concept of the blow-fill-seal technique is that a container is formed, filled and sealed in a continuous process without manual intervention in a sterile and closed area within a machine. Therefore, the blow-fill-seal technique is suitable for the aseptic production of sterile dosage forms of medical liquids. The blow-fill-seal technique is multi-stage: typically, a tubular preform is first formed by extrusion. This extruded tube is then enclosed in a mould. After shaping the container by inflating it in the mould, the container is filled with liquid via a mandrel. The container is then sealed. All steps take place in a sterile area of the machine.

The blow-fill-seal technique is a robust method for the aseptic preparation of sterile medicinal products.

BRIEF DESCRIPTION OF THE DRAWING FIGURES

Further features, expediencies and advantages of the invention are described below by means of exemplary embodiments with reference to the attached figures.

DETAILED DESCRIPTION

Figure 1:
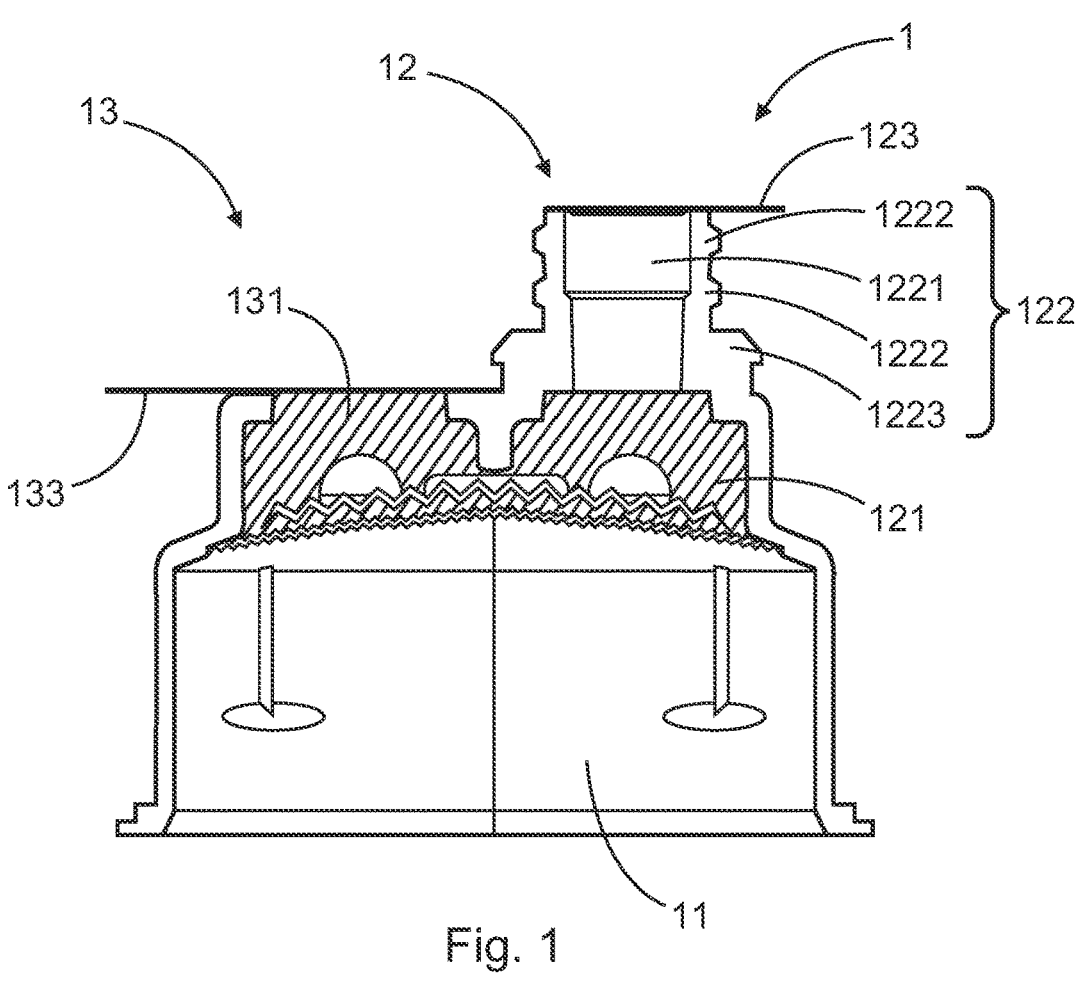
FIG. 1 shows a sectional view of a cap of a system according to an embodiment of the invention.
Figure 3:
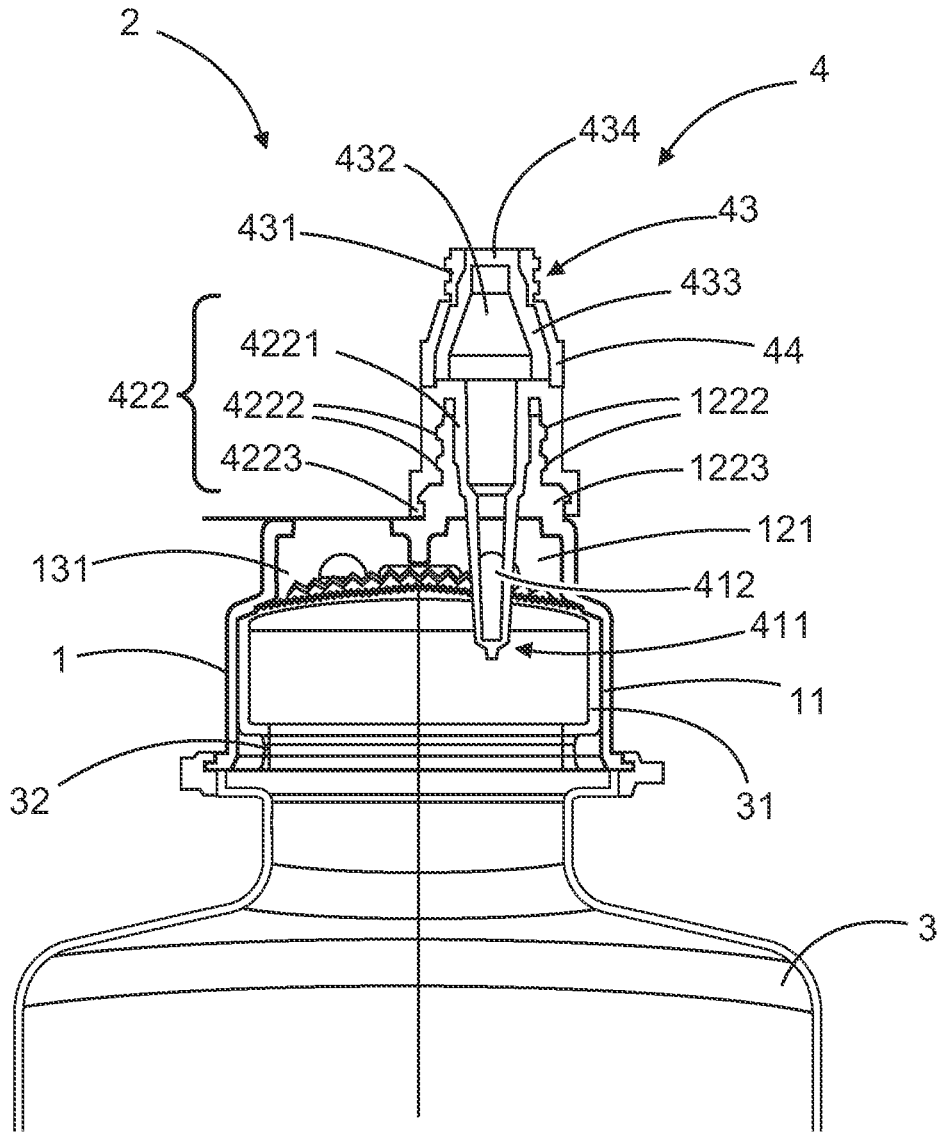
FIG. 3 shows a sectional view of a medical fluid container according to another embodiment of the invention with the system comprising the cap shown in FIG. 1 and the attachment part shown in FIG. 2.

In FIG. 1, the cap 1 of the system according to an embodiment of the invention is shown in a sectional view. Further details of the cap 1 become apparent from FIG. 3, in which the medical fluid container 2 according to an embodiment of the invention is shown. The medical fluid container 2 comprises a hollow body 3 to which the cap 1 is attached. In FIG. 3, the medical fluid container 2 including the cap 1 and the attachment part 4 is shown in sectional view.

The cap 1 comprises a mounting area 11 which serves to attach the cap 1 to the head area 31 of the hollow body 3. In the embodiments shown in the figures, the mounting portion 11 has a helmet-like shape configured to receive the head portion 31 of the hollow body 3 therein such that the cap 1 tightly encloses the head portion 31. Preferably, this is achieved by forming the cap 1 onto the head portion 31 by injection moulding, i.e. forming at least part of the structure of the cap 1 by injection moulding such that this part is firmly attached to the head portion 31 after moulding. For example, injection moulding may be used to form a housing of the cap 1 (i.e. in FIGS. 1 and 3 the cap 1 excluding the septa 121, 131 described further below and excluding the covers 123, 133), wherein the housing has recesses into which the septa 121, 131 are inserted.

The cap 1 comprises a first port 12 suitable for providing a fluid connection between the fluid container 2 and an external device. The external device may be a device for withdrawing fluid from the fluid container and/or a device for supplying fluid to the fluid container. For example, the external device is a hypodermic syringe. The first port 12 comprises a septum 121. The septum 121 of the first port 12 comprises an elastomer, for example rubber or synthetic rubber. The first port 12 further comprises a connection structure 122. The connection structure 122 is configured to be connected—in a releasable or non-releasable manner—to a complementary connection structure 422 of an attachment part 4, which comprises a hollow spike 41 and a joining structure 43 in fluid communication with the hollow spike 41, such that the hollow spike 41 pierces the septum 121 of the first port 12. The attachment part 4 is described in more detail below. In the embodiments shown in the figures, the connection structure 122 comprises an internal cone 1221, an externally threaded structure 1222 and a circumferential protrusion 1223 having a hook-shaped cross-section. The internal cone 1221 is preferably configured as a female Luer cone. The external threaded structure 1222 may comprise continuous threads or protrusions forming a thread. The circumferential protrusion 1223 provides an element of an engagement connection. In alternative embodiments not shown in the figures, the connection structure 122 is formed in a different manner. For example, the connection structure may consist of an internal cone or an external cone alone. Additionally, it may comprise a threaded structure. Alternatively or additionally, it may comprise protruding and/or recessed structures as elements of an engagement connection. Engagement structures may also be absent in other embodiments.

In the embodiments shown in the figures, the cap 1 comprises a second port 13. The second port 13 comprises a septum 131. In the embodiments shown in the figures, the second port does not comprise a connection structure analogous to the connection structure 122 of the first port 12. Via the second port 13, a further fluid connection can be made between the fluid container 2 and an external device for withdrawing fluid from the fluid container 2 and/or for supplying fluid to the fluid container 2. For this purpose, the septum 131 of the second port 13 is pierced by a piercing device of this external device.

In further embodiments not shown in the figures, the second port 13 comprises a connection structure analogous to the connection structure 122 of the first port 12.

In further embodiments not shown in the figures, no second port is provided.

In further embodiments not shown in the figures, the cap 1 comprises at least one further port in addition to the first port 12 and the second port 13.

Preferably, each port of the cap 1 is protected from contamination by a cover. In particular, the cover maintains a sterile condition of the outer surface of the septum. Preferably, the cover is removed before the port is connected to the attachment part 4 or to the piercing device of the external device. In the embodiments shown in the figures, each cover is a sealing film 123, 133 being attached by gluing or welding, which is peeled off by hand by the user before piercing the respective septum.

Before the hollow spike 41 of the attachment part 4 or the piercing device of an external device for fluid withdrawal or fluid addition is pierced into a septum 121, 131 of one of the ports 12, 13 for the first time, the head area 31 of the hollow body preferably comprises a closed wall such that the hollow body 3 itself is a sealed hollow body which is not closed by the cap 1.

The hollow body 3 is preferably a hollow body made of plastic, more preferably of a polyolefin, even more preferably of polyethylene, most preferably of PE-LD.

In the embodiments shown in the figures, the hollow body 3 comprises a head portion 31 and a neck portion 32 with a smaller diameter compared to the head portion 31. This geometry improves the secure attachment of the cap 1 to the head portion 31. Preferably, the cap 1 is attached to the hollow body 3 by forming the cap 1 onto the head portion 31 of the hollow body 3 by injection moulding. The term "forming" in this context means that the cap 1 is not prefabricated, but is directly formed in place on the head portion 31 of the hollow body 3. Alternatively, it is also possible to prefabricate the cap 1 and attach it to the head region 31 of the hollow body 3, for example by welding, gluing or another suitable joining method.

The septa 121, 131 may be formed by injection moulding. Most preferably, two-component injection moulding is used to form the housing of the cap 1 from a first material component and to form the septa 121, 131 from a second material component by injection moulding.

Figure 2:
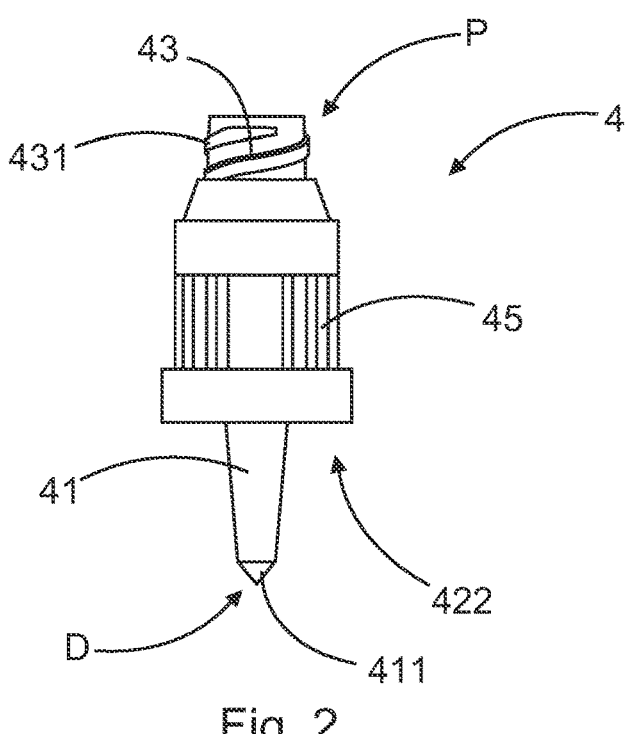
FIG. 2 shows a perspective view of an attachment part of the system according to the embodiment.

In FIG. 2, the attachment part 4 of the system according to the embodiment of the invention is shown in perspective view, wherein the attachment part 4 is neither connected to the cap 1 nor to a device for supplying or withdrawing a fluid. The cap 1 and the attachment part 4, which are each shown separately in FIGS. 1 and 2, together form the system according to the embodiment. Further details of the attachment part 4 are shown in FIG. 3, in which the attachment part 4, which is connected to the cap 1 connected to a hollow body 3, is shown in sectional view.

The attachment part 4 comprises a hollow spike 41, a complementary connection structure 422 and a joining structure 43.

The hollow spike 41 is configured to pierce a septum. The hollow spike comprises a tip 411 at its distal end (D) and a fluid channel 412 in its interior. The hollow spike 41 and the complementary connection structure 422 are arranged such that the hollow spike 41 pierces the septum 121 of the first port 12 when the attachment part 4 is connected to the cap 1 by connecting, i.e. engaging, the connection structure 122 and the complementary connection structure 422.

The complementary connection structure 422 is configured to be connected to the connection structure 122 of the cap 1. Therefore, the connection structure 122 and the complementary connection structure 422 are adapted to be connected to each other in such a way that a releasable or non-releasable connection is possible, i.e. the complementary connection structure 422 must be complementary to the connection structure 122 in this sense such that they can be engaged with each other. In the embodiments shown in the figures, the complementary connection structure 422 comprises an external cone 4221 complementary to the internal cone 1221 of the connection structure 122, an internal threaded structure 4222 complementary to the external threaded structure 1222 of the connection structure 122, and a recess 4223 complementary to the peripheral protrusion 1223 of the connection structure 122. The external cone 4221 is preferably configured as a male Luer cone. Herein, the internally threaded structure 4222 may comprise continuous threads or threaded sections. The circumferential recess 4223, together with the circumferential projection 1223, provides an engagement connection. In alternative embodiments not shown in the figures, the complementary structure 422 is formed corresponding to a connection structure 122 configured in a different manner. In this context, reference is made to the above description of alternative embodiments of the connection structure.

The joining structure 43 is configured for connecting an external device for taking fluid out of the fluid container 2 and/or a device for bringing fluid into the fluid container 2.

For this purpose, in the embodiments shown in the figures, the joining structure 43 has an external thread 431 and a sealing element 432. An internal thread of the external device for withdrawing fluid from the fluid container 2 and/or a device for supplying fluid into the fluid container 2 can be screwed onto the external thread 431. The sealing element 432 is configured to receive the end of a fluid channel or a joining piece of the external device. The joining piece may in particular be a male Luer cone. This is the case, for example, if a hypodermic syringe without a hypodermic needle attached thereto is used as an external device for withdrawing fluid from the fluid container 2 and/or a device for supplying fluid to the fluid container 2. Specifically, the sealing element 432 is configured as a slit valve. The slit valve comprises a body 433 made of an elastic material, which is fitted into a housing portion 44 of the attachment part 4 and which comprises a slit 434 at its proximal end. Through the slit 434, the end of the fluid channel or the joining piece of the external device can be inserted without having to pierce the sealing element. Before the end of the fluid channel or the joining piece has been inserted into the slit and after the end of the fluid channel or the joining piece has been withdrawn from the slit again, the slit 434 is closed, i.e. the cut surfaces of the slit 434 seal against each other such that the slit valve closes the joining structure 43 in a fluid-tight manner.

The housing portion 44 with the joining structure 43 may, for example, be welded onto the remaining attachment part 4 or integrally connected thereto.

Preferably, a continuous fluid channel extends through the attachment part 4, i.e. a fluid channel that extends from a distal end (D) of the hollow spike 41 to a proximal end (P) of the joining structure 43.

To make the attachment part 4 as ergonomic as possible for its connection to the cap 1, a grip structure 45 may be provided on its outer surface, for example in the form of grooves, protrusions or a roughened area.

The designation "external device" expresses that this device for fluid withdrawal or fluid addition is not considered as part of the system according to the invention comprising the cap 1 and the attachment part 4 and not as part of the medical fluid container according to the invention.

When, on the one hand, the external device for withdrawing fluid from the fluid container 2 and/or for supplying fluid into the fluid container 2 is connected to the attachment part 4 and, on the other hand, the attachment part 4 is connected to the first port 12 of the cap 1 attached to a hollow body 3, a fluid connection is consequently provided between the fluid container 2 and the external device. This is then achieved in an indirect manner, i.e. the fluid connection is then effectuated by the attachment part 4.

When a piercing device of an external device is used to pierce the septum 121 of the first port 12 to withdraw fluid from the fluid container 2 and/or to supply fluid to the fluid container 2, then a fluid connection is hereby provided between the fluid container 2 and the external device. This is then achieved in a direct manner, i.e. the fluid connection is provided without interposition of the attachment part 4.

In operation, if the attachment part 4 and the cap 1 are not already connected, the attachment part 4 is connected by the user to the first port of the cap 1 by engaging the connection structure 122 with the complementary connection structure 422. Herein, the cap 1 is attached to a hollow body 3. Depending on the configuration of the connection structure 122 and the complementary connection structure 422, the attachment part 4 is screwed onto the cap 1, plugged onto the cap 1 or otherwise connected to the cap 1. For example, the thread 4222 of the attachment part 4 is screwed onto the thread 1222 of the connection structure until resilient engagement structures (for example in the form of the projection 1222 and the recess 4222) engage with each other. Preferably, the engagement structures are configured such that the engagement is audible and/or tactile such that the completion of the engagement can be easily determined. When connecting the connection structure 122 to the complementary connection structure 422, the hollow spike 41 penetrates the septum 121 of the first port 12 and the wall of the head region 31 of the hollow body 3 with the aid of the tip 411. At least the tip 411 of the hollow spike 41 then protrudes into the interior of the hollow body 3, causing the attachment part 4 to be in fluid communication with the interior of the hollow body and the joining structure 43 to allow connection of an external device to withdraw a fluid from the hollow body 3 and/or to introduce a fluid into the interior of the hollow body.

It is possible that the medical fluid container 2 is commercialised in such a way that the attachment part 4 is already connected to the connection structure 122. However, it is also possible that the connection of the attachment part 4 to the connection structure 122 is left to the user.

Figures 4, 5:
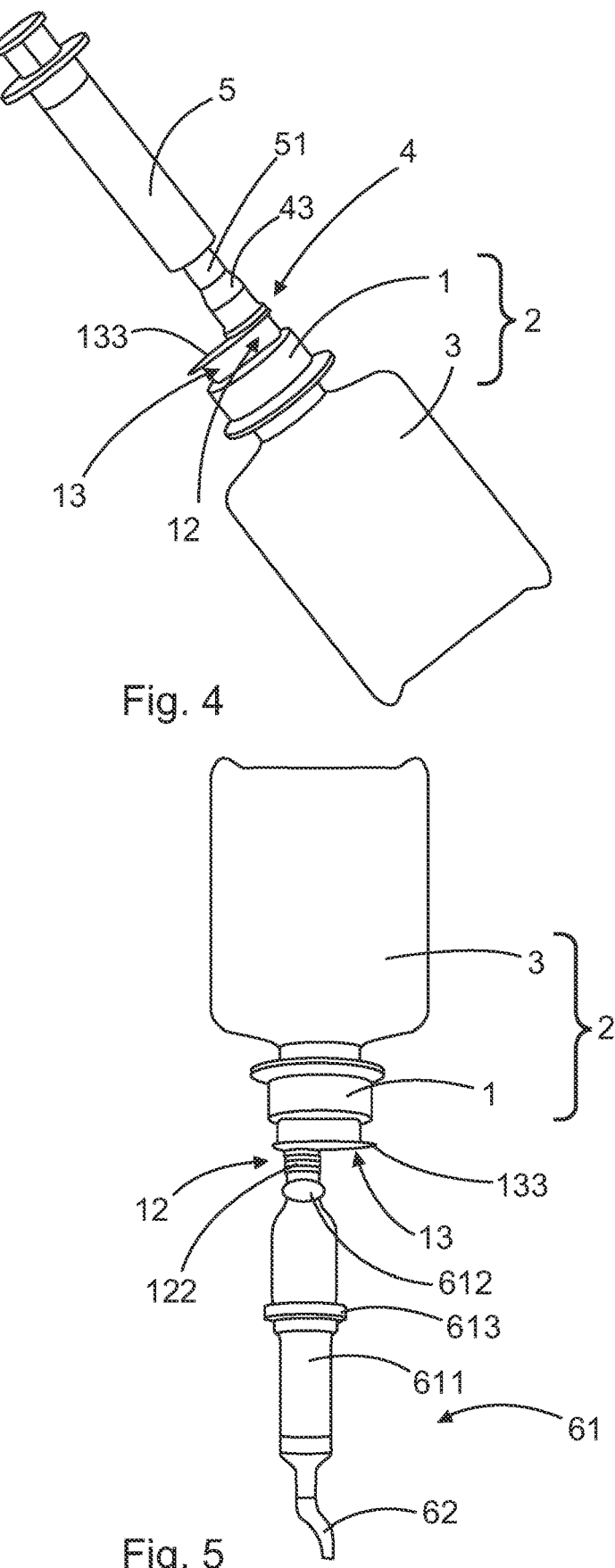
FIG. 4 shows a perspective view of the medical fluid container according to the embodiment, to which a device for fluid withdrawal or fluid addition is connected.
FIG. 5 shows a perspective view of the medical fluid container according to the invention, to which another device for fluid withdrawal is connected without using the attachment part.

To supply a fluid into the medical fluid container 2 or to withdraw a fluid from the medical fluid container 2 via the first port 12, the user may, for example, connect a hypodermic syringe 5 with a female Luer lock thread 51 to the joining structure 43 of the attachment part 4 as an external device for fluid withdrawal or fluid supply by screwing the female Luer lock thread 51 of the hypodermic syringe 5 to the male thread 431 of the joining structure 43. In doing so, the male Luer cone of the hypodermic syringe 5 is inserted into a corresponding receiving portion of the joining structure 43, such as the slit 434 of a slitted valve. The desired fluid connection is then established between the hypodermic syringe 5 and the interior of the hollow body 3 of the medical fluid container 2. This situation is illustrated in FIG. 4.

In addition to the possibility of connecting an external device for supplying and/or withdrawing a fluid (in the case of the example shown in FIG. 4 a hypodermic syringe 5) to the first port 12 without piercing a septum, there is also the possibility of connecting another external device for supplying and/or withdrawing a fluid with a piercing device to the first port 12 by piercing the septum 121 of the first port 12 with the piercing device according to the invention. This situation is illustrated in FIG. 5 using, as an example, an infusion set 6 with a drip chamber 61 and an infusion tube 62 connected thereto. The drip chamber 6 has a hollow chamber 611, a ventilation valve 612, a grip ring 613 and a piercing device configured as a hollow spike at its upper end in FIG. 5 (not shown in FIG. 5). The hollow spike of the drip chamber 6 is used to pierce the septum 121 of the first port 12 to establish the desired fluid connection between the infusion set 6 and the interior of the hollow body 3 of the medical fluid container 2. Herein, no attachment part 4 is connected to the connection structure 122 of the first port 12. In other words, in one embodiment, the system according to the invention may allow the first port 12 of the cap 1 to be used not only together with the attachment part 4, but also together with a suitable device for withdrawing or supplying fluid but without the attachment part 4. The system according to the invention therefore allows a very variable use, for example of a medical fluid container for an infusion fluid or other medical fluid. In this paragraph, the connection of the first port 12 to an infusion set comprising a piercing device is described, wherein the attachment part is not used. However, an infusion set 6 may also be connected to the attachment part 4, wherein the latter is connected to the cap 1. When the connection of the infusion set 6 to the joining structure 43 of the attachment part is intended, an infusion set is used which comprises, instead of or in addition to the piercing device, a structure which can be engaged with the joining structure 43.

In the above embodiments of the system according to the invention comprising the cap 1 and the attachment part 4 as well as in the above embodiments of the medical fluid container 2 according to the invention, the septum 121 of the first port 12 is preferably made of a material comprising a silicone, further preferably made of a silicone.

Additionally or alternatively, in the above embodiments of the system according to the invention comprising the cap 1 and the attachment part 4 as well as in the above embodiments of the medical fluid container 2 according to the invention, in which the cap 1 comprises a second port 13, the septum 131 of the second port 13 is preferably made of a material comprising a silicone, further preferably made of a silicone.

In the above embodiments of the system according to the invention comprising the cap 1 and the attachment part 4 as well as in the above embodiments of the medical fluid container 2 according to the invention, all other parts of the cap 1, i.e. all parts of the cap 1 other than a septum, are preferably made of a material comprising a polyolefin, more preferably made of a polyolefin.

In the above embodiments of the system according to the invention comprising the cap 1 and the attachment part 4 as well as in the above embodiments of the medical fluid container according to the invention, the attachment part 4 is preferably made of a material comprising a polyolefin, further preferably made of a polyolefin.

In accordance with this preferred choice of materials, the method according to the invention for manufacturing a fluid container, preferably a material comprising a silicone, further preferably consisting of a silicone, is used for forming the septum 121 of the first port 12.

In accordance with this preferred choice of materials, the method according to the invention for manufacturing a fluid container, preferably a material comprising a silicone, further preferably consisting of a silicone, is used for forming the septum 131 of the second port 13.

In accordance with this preferred choice of materials, in the method according to the invention for producing a fluid container for forming the remaining parts of the cap 1, i.e. in particular for forming the cap 1 on a region 31 of the hollow body 3, preferably a material is used which comprises a polyolefin, further preferably consists of a polyolefin.

The invention claimed is:

1. A system comprising:
a cap for a medical fluid container; and
an attachment part,
the cap comprising at least a first port for providing a fluid connection between the fluid container and a device,
the device being configured for withdrawing fluid from the fluid container and/or for supplying fluid into the fluid container,
the first port comprising a first septum and a connection structure,
the attachment part comprising a hollow spike and a joining structure in fluid communication with the hollow spike,
the joining structure being configured to connect the device to the fluid container,
the connection structure configured to be connected to a complementary connection structure of the attachment part in a releasable or non-releasable manner such that the hollow spike pierces the first septum,
wherein the connection structure comprises a valve.

2. The system according to claim 1,
wherein the connection structure comprises a cone.

3. The system according to claim 2, wherein the connection structure comprises a threaded structure and/or an engagement structure configured to become engaged or to be engaged with a complementary threaded structure or a complementary engagement structure, respectively, of the attachment part in order to connect the connection structure to the attachment part.

4. The system according to claim 3,
wherein the cap further comprises a second port,
wherein the second port comprises a septum, and
wherein the joining structure comprises a cone.

5. The system according to claim 1, wherein the cap further comprises a second port and the second port comprises a second septum.

6. The system according to claim 1, wherein a through fluid channel extends from a distal end of the hollow spike to the joining structure.

7. The system according to claim 1, wherein the joining structure comprises a cone.

8. The system according to claim 1, wherein the joining structure comprises a thread.

9. The system according claim 1, wherein the valve is configured as a slit valve.

10. A medical fluid container comprising:
the system according to claim 5; and
a hollow body.

11. The medical fluid container according to claim 10, wherein:
the hollow body is sealed in a fluid-tight manner, and/or the hollow body is collapsible.

12. The medical fluid container according to claim 10, wherein the hollow body is a hollow plastic body.

13. The medical fluid container according to claim 12, wherein at least a wall of the hollow body is formed of polyethylene.

14. The medical fluid container according to claim 10, wherein the cap is formed by injection molding onto a portion of the hollow body.

15. The medical fluid container according to claim 14, wherein at least one of the first septum and the second septum is formed by injection moulding onto the portion of the hollow body.

16. The medical fluid container according to claim 15, wherein the cap and at least one of the first septum and the second septum are formed by two-component injection molding.

17. The medical fluid container according to claim 10, wherein the cap is configured and arranged on the hollow body such that the hollow spike pierces the first septum and a portion of a wall of the hollow body when the attachment part is connected to the connection structure.

18. The medical fluid container according to claim 17, wherein at least one of the first port and the second port is sealed in a sterile manner.

19. The medical fluid container according to claim 10,
wherein the hollow body is a hollow plastic body,
wherein the hollow body is sealed in a fluid-tight manner,
wherein the hollow body is collapsible, and
wherein the cap is configured and arranged on the hollow body such that the hollow spike pierces the first septum of the first port and a portion of a wall of the hollow body when the attachment part is connected to the connection structure.

* * * * *